(12) United States Patent
Myers et al.

(10) Patent No.: US 7,556,944 B2
(45) Date of Patent: Jul. 7, 2009

(54) METHODS AND COMPOSITIONS FOR USE IN PREPARING SIRNAS

(75) Inventors: Jason Myers, Concord, CA (US); James Ferrell, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 578 days.

(21) Appl. No.: 10/427,758

(22) Filed: Apr. 30, 2003

(65) Prior Publication Data

US 2003/0224432 A1      Dec. 4, 2003

Related U.S. Application Data

(60) Provisional application No. 60/400,655, filed on Aug. 1, 2002, provisional application No. 60/377,704, filed on May 3, 2002.

(51) Int. Cl.
*C12P 19/34* (2006.01)
*C07H 21/02* (2006.01)
*C07H 21/04* (2006.01)
*C12Q 1/68* (2006.01)
*C12N 5/00* (2006.01)

(52) U.S. Cl. .................. 435/91.3; 435/6; 435/91.1; 536/23.1; 536/24.1; 536/24.5

(58) Field of Classification Search .................. None
See application file for complete search history.

(56) References Cited

U.S. PATENT DOCUMENTS

2002/0162126 A1* 10/2002 Beach et al. .................. 800/8

2003/0044941 A1* 3/2003 Crooke ........................ 435/91.2
2003/0108923 A1   6/2003 Tuschl et al.
2008/0132461 A1   6/2008 Tuschl et al.

OTHER PUBLICATIONS

Ketting et al. Dicer Functions in RNA Interference and in Synthesis of Small RNA Involved in Developmental Timing in C.elegans. Genes & Development Oct. 15, 2001, vol. 15, No. 20 pp. 2654-2659.
Ambros et al. Dicing up RNAs, Science Aug. 3, 2001, vol. 293, pp. 811-812.
Zhang et al. "Human Dicer Preferentially Cleaves dsRNAs at Their Termini Without A Requirement for ATP" The EMBO Journal. Nov. 1, 2002, vol. 21, No. 21, pp. 5875-5885.
Bernstein et al. "Role for a bidentate ribonuclease in the initiation step of RNA interference" NATURE, vol. 409, Jan. 18, 20001, pp. 363-366.
Elbashir et al. "Duplexes of 21-nucleotide RNAs mediate RNA interference in cultured mammalian cells" NATURE, vol. 411, May 24, 2001, pp. 494-498.
Yang et al. "Short RNA duplexes produced by hydrolysis with *Escherichia coli* RNase III mediate effective RNA interference in mammalian cells" PNAS, Jul. 23, 2002, vol. 99. No. 15, 9942-9947.

* cited by examiner

*Primary Examiner*—Sean R McGarry
(74) *Attorney, Agent, or Firm*—Bozicevic, Field & Francis LLP; Bret E. Field

(57) ABSTRACT

Methods and compositions for producing siRNAs, e.g., in the form of a d-siRNA composition, from dsRNAs are provided. In the subject methods, a dsRNA is contacted with a composition that includes an activity that cleaves dsRNA into siRNAs, where the composition efficiently cleaves dsRNA into siRNAs. siRNAs produced by the subject methods find use in a variety of applications, particularly in applications where the specific reduction or silencing of a gene is desired. Also provided are kits for use in practicing the subject invention.

14 Claims, 5 Drawing Sheets

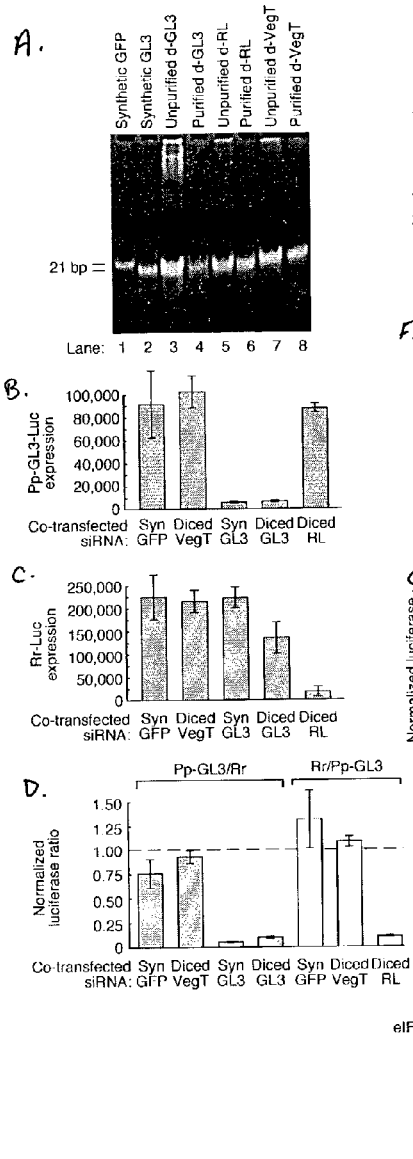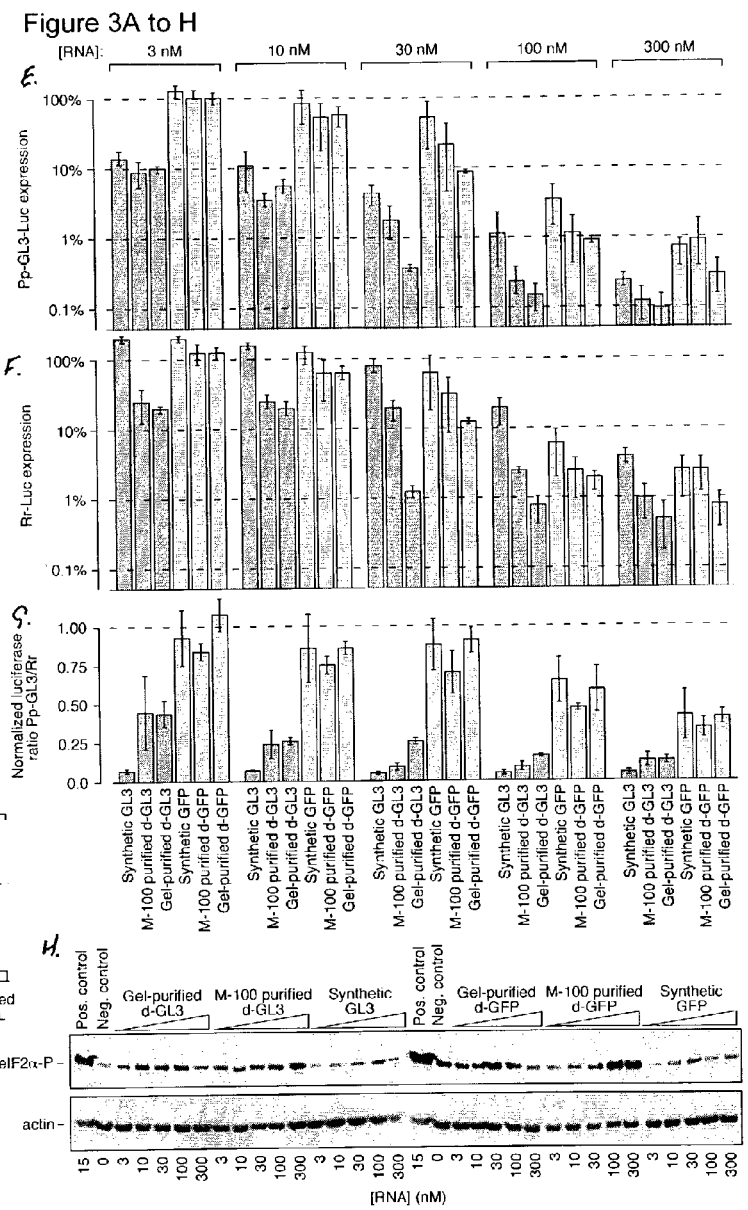
Figure 3A to H

Figure 4A to B
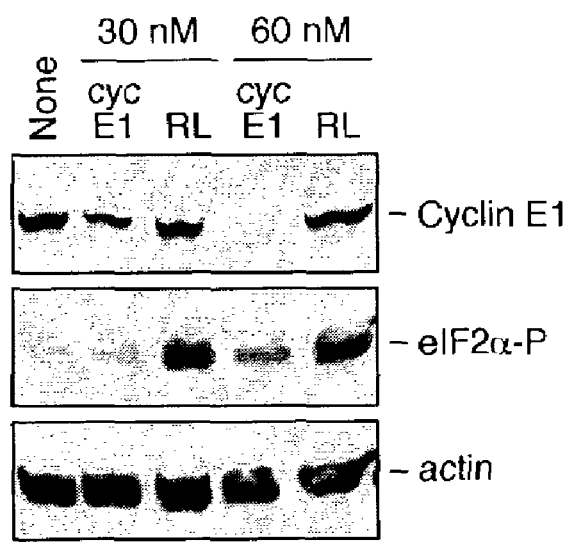
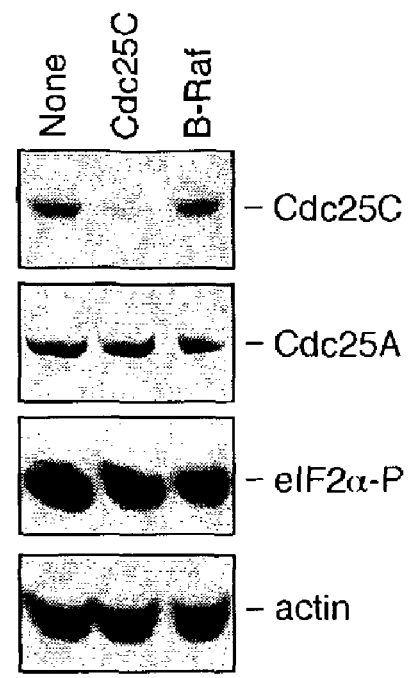

SEQUENCE LISTING

```
<160> NUMBER OF SEQ ID NOS: 5
<210> SEQ ID NO 1
<211> LENGTH: 21
<212> TYPE: DNA
<213> ORGANISM: bacteriophage

<400> SEQUENCE: 1
gcgtaatacg actcactatg g                                              21

<210> SEQ ID NO 2
<211> LENGTH: 22
<212> TYPE: DNA
<213> ORGANISM: bacteriophage

<400> SEQUENCE: 2
gcgaattaac cctcactaaa gg                                             22

<210> SEQ ID NO 3
<211> LENGTH: 22
<212> TYPE: DNA
<213> ORGANISM: bacteriophage

<400> SEQUENCE: 3
gcgatttagg tgacactata ga                                             22

<210> SEQ ID NO 4
<211> LENGTH: 43
<212> TYPE: DNA
<213> ORGANISM: bacteriophage

<400> SEQUENCE: 4
gcgtaatacg actcactata ggagagagac acttcctta ccg                       43

<210> SEQ ID NO 5
<211> LENGTH: 43
<212> TYPE: DNA
<213> ORGANISM: bacteriophage

<400> SEQUENCE: 5
gcgtaatacg actcactata ggtataggcc acttctgctc acc                      43
```

METHODS AND COMPOSITIONS FOR USE IN PREPARING SIRNAS

CROSS-REFERENCE TO RELATED APPLICATIONS

This application claims priority (pursuant to 35 U.S.C. § 119 (e)) to the filing date of the U.S. Provisional Patent Application Ser. No. 60/400,655 filed Aug. 1, 2002 and U.S. Provisional Patent Application Ser. No. 60/377,704 filed May 3, 2002; the disclosures of which are herein incorporated by reference.

GOVERNMENT RIGHTS

This invention was made with Government support under contract GM46383 awarded by the National Institutes of Health. The Government has certain rights in this invention.

INTRODUCTION

1. Field of the Invention

The field of this invention is genomics.

2. Background of the Invention

RNAi has become the method of choice for loss-of-function investigations in numerous systems including, C. elegans, Drosophila, fungi, plants, and even mammalian cell lines. To specifically silence a gene in most mammalian cell lines, small interfering RNAs (siRNA) are used because large dsRNAs (>30 bp) trigger the interferon response and cause nonspecific gene silencing. Currently, siRNAs are produced by chemical synthesis, by in vitro transcription from a short DNA template, or by transfection of DNA plasmids that give rise to hairpin RNAs in vivo.

All of these approaches are capable of gene silencing, but not without problems. First, the chemical synthesis of siRNAs is very expensive. The current price of a single custom-synthesized siRNA is several hundred dollars, and three to eight siRNAs may be required to attain a high probability of silencing any particular gene. In addition, the rules for what makes an effective siRNA are not well worked out, and consequently there is a substantial chance that any single 21 nucleotide region selected from the mRNA will be ineffective in initiating mRNA cleavage or inhibiting translation. In vitro transcribed-siRNAs and plasmid-encoded hairpin-siRNAs are less expensive, but like chemical synthesis there is a chance that the 21-nucleotide target will be ineffective for gene silencing. Moreover, such methods do not scale up easily for screens, since for each member of the library, one or more oligonucleotides would need to be individually designed and synthesized. In addition, single siRNAs cause cleavage of the target mRNA at a single site, opening the possibility that the remaining 3'-fragment will be translated. The resulting N-terminal truncated protein may act as a dominant negative or constitutively active protein rather than as a true protein-null. An inexpensive, efficient method for generating a large number of different siRNAs from any given mRNA or from a mix of mRNAs would obviate these problems.

In order to improve the efficacy of RNAi use in mammalian cell lines, an inexpensive and efficient method of generating a large number of different siRNAs is needed. The present invention satisfies this need.

Relevant Literature

Published PCT applications of interest include WO 01/68836.

SUMMARY OF THE INVENTION

Methods and compositions for producing siRNAs, e.g., in the form of a d-siRNA composition, from dsRNAs are provided. In the subject methods, a dsRNA is contacted with a composition that includes an activity that cleaves dsRNA into siRNAs, where the composition efficiently cleaves dsRNA into siRNAs. siRNAs produced by the subject methods find use in a variety of applications, particularly in applications where the specific reduction or silencing of a gene is desired. Also provided are kits for use in practicing the subject invention.

BRIEF DESCRIPTION OF THE FIGURES

FIG. 1A: Analysis of r-Dicer expression and in vitro activity. Lysates from uninfected and Dicer-infected Hi5 cells were fractionated on a cobalt-Sepharose affinity resin. The upper panels are from a Coomassie-stained gel showing the 225 kDa Dicer protein and other proteins present in the various purification fractions. The middle panels are from an immunoblot with an anti-T7-epitope antibody that recognizes the tag at the N-terminus of r-Dicer. The bottom panels are from an ethidium-stained native polyacrylamide gel showing the 500 bp dsRNA Dicer substrate and the 22 bp d-siRNAs produced by active r-Dicer. FIG. 1B: Copurification of r-Dicer protein and activity on Q-Sepharose. Affinity-purified r-Dicer was further purified on Q-Sepharose and assayed for r-Dicer protein (upper panel) and activity (bottom panel). FIG. 1C: Cofactor requirements and substrate specificity of r-Dicer. r-Dicer was incubated with under standard reaction conditions with 500 bp dsRNA, a 500 bp ssRNA, or a 600 bp dsDNA (lanes 1-3). r-Dicer was also incubated with 500 bp dsRNA with various additions to (RNasin) or omissions from (ATP and or $Mg^{2+}$) the reaction mix (lanes 4-7).

FIGS. 3A to H. d-siRNAs specifically silence luciferase expression in HEK 293 cells. (A) Quantity, quality and purity of siRNAs and d-siRNAs. Various ~500 bp dsRNAs were cleaved by r-Dicer to generate d-siRNAs. The contaminating reaction components and ~500 bp dsRNA were separated from the d-siRNAs by a series of spin columns. Chemically synthesized siRNAs (lanes 1 and 2), purified d-siRNAs (lanes 4, 6, and 8) and a portion of the unpurified dicing reaction (lanes 3, 5, and 7) were electrophoresed on a 15% native polyacrylamide gel. RNAs were visualized by staining with ethidium bromide. (B, C) Absolute firefly and Renilla luciferase activity. Firefly (Photinus pyralis, Pp-luc, GL3) and sea pansy (Renilla reinformis, Rr-luc, RL) luciferase expression vectors were cotransfected with various siRNAs or d-siRNAs (30 mmol per L medium). The firefly (B) and Renilla (C) luciferase activities were determined individually. (D) Normalized luciferase activity. Either the Pp-luc/Rr-luc (grey bars) or the Rr-luc/Pp-luc ratio (white bars), depending on which luciferase was the target, was calculated. The plotted data was averaged from three independent experiments±S.E. (E-G) Absolute (E, F) and normalized (G) firefly and Renilla luciferase activity. The firefly (Photinus pyralis, Pp-luc, GL3) and sea pansy (Renilla reinformis, Rr-luc, RL) luciferase expression vectors were cotransfected with either various concentrations of GL3 or GFP siRNAs or d-siRNAs. Concentrations were taken as nmol per L of medium. The firefly (E) and Renilla (F) luciferase activities were determined individually (dark gray bars indicate cells transfected with siRNAs or d-siRNAs targeting GL3; light gray bars indicate cells transfected with an irrelevant GFP siRNA or d-siRNA). The Pp-luc/Rr-luc ratio (G) was calculated for cells transfected with GL3 siRNAs or d-siRNAs (dark gray bars) and for cells transfected with irrelevant GFP siRNAs or d-siRNAs (light gray bars). The plotted data was averaged from three independent experiments±S.E. (H) eIF2α phosphorylation in cells treated with synthetic and diced siRNAs. The various cellular lysates were subjected to immunoblotting for eIF2α phosphorylation (top) or, as a loading control, actin (bottom). "Positive control" denotes cells treated with 15 nM 500 bp dsRNA; "negative control" denotes untreated cells.

FIGS. 4A to B. d-siRNAs can silence endogenous genes. (A) Cyclin E1 is silenced in a dose dependent fashion. HEK 293 cells were transfected with two different pools of d-siRNAs, one complementary to cyclin E1 and another to Renilla luciferase. After 72 h, cells were lysed and subjected to immunoblotting with various antibodies. (B) Cdc25C d-siRNAs silence Cdc25C expression without affecting Cdc25A expression. HEK 293 cells were transfected for 72 h with two different pools of d-siRNAs, one complementary to Cdc25C and another to B-Raf. Immunoblotting shows amounts of the Cdc25C, Cdc25A, actin (loading control), and phospho-eIF2α.

DEFINITIONS

Figure 1A:
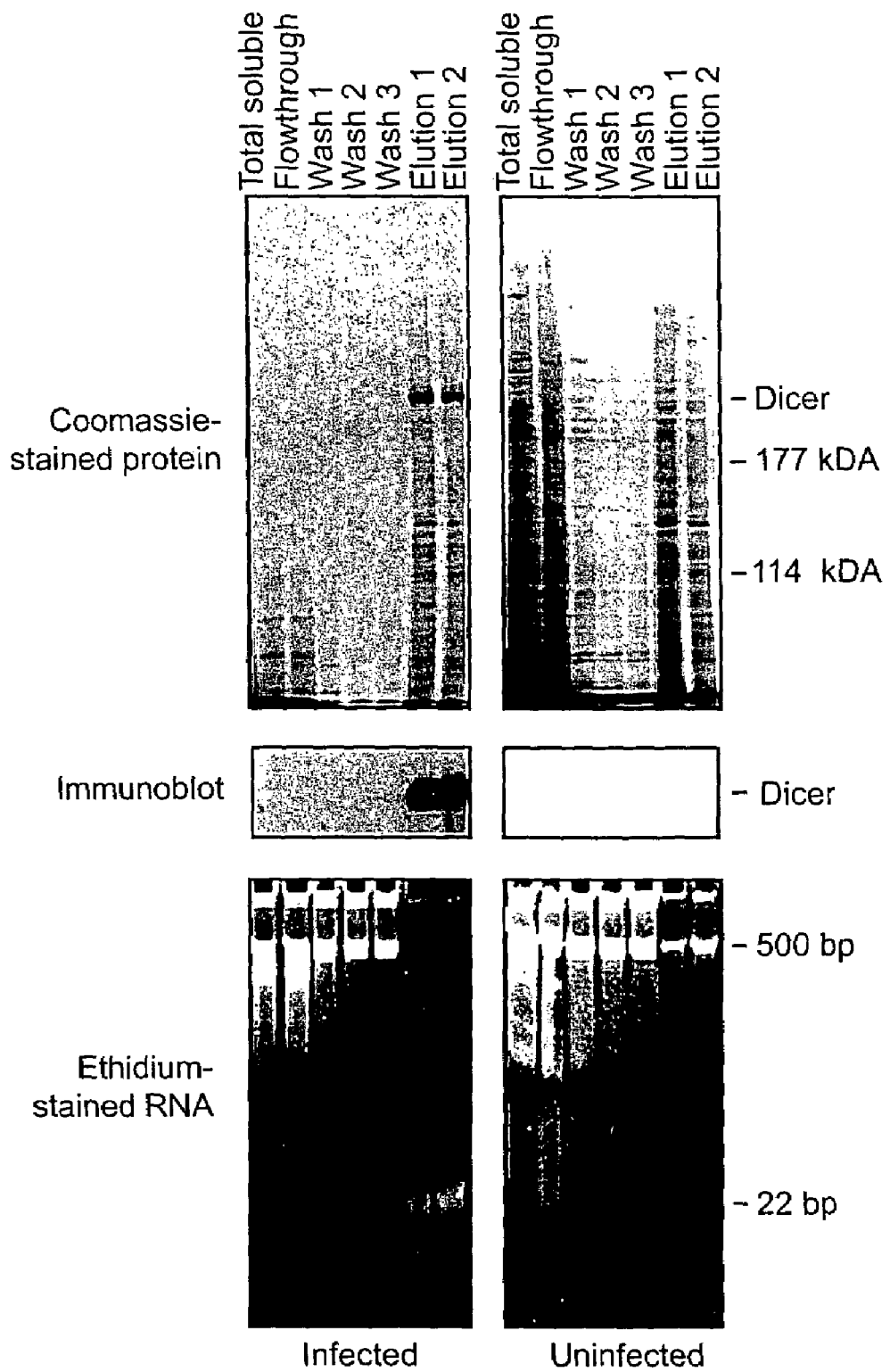
FIGS. 1A to 1C. r-Dicer activity in vitro.

For convenience, certain terms employed in the specification, examples, and appended claims are collected here.

As used herein, the term "vector" refers to a nucleic acid molecule capable of transporting another nucleic acid to which it has been linked. One type of vector is a genomic integrated vector, or "integrated vector", which can become integrated into the chromsomal DNA of the host cell. Another type of vector is an episomal vector, i.e., a nucleic acid capable of extra-chromosomal replication. Vectors capable of directing the expression of genes to which they are operatively linked are referred to herein as "expression vectors". In the present specification, "plasmid" and "vector" are used interchangeably unless otherwise clear from the context.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, that may optionally include intron sequences that are derived from chromosomal DNA. The term "intron" refers to a DNA sequence present in a given gene that is not translated into protein and is generally found between exons. As used herein, the term "transfection" means the introduction of a nucleic acid, e.g., an expression vector, into a recipient cell by nucleic acid-mediated gene transfer.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

Likewise, "encodes", unless evident from its context, will be meant to include DNA sequences that encode a polypeptide, as the term is typically used, as well as DNA sequences that are transcribed into inhibitory antisense molecules.

The term "loss-of-function", as it refers to genes inhibited by the subject RNAi method, refers a diminishment in the level of expression of a gene when compared to the level in the absense of dsRNA constructs.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence. "Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

By "recombinant virus" is meant a virus that has been genetically altered, e.g., by the addition or insertion of a heterologous nucleic acid construct into the particle.

As used herein, the terms "transduction" and "transfection" are art recognized and mean the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a dsRNA construct.

"Transient transfection" refers to cases where exogenous DNA does not integrate into the genome of a transfected cell, e.g., where episomal DNA is transcribed into mRNA and translated into protein.

A cell has been "stably transfected" with a nucleic acid construct when the nucleic acid construct is capable of being inherited by daughter cells.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences can be directly or indirectly regulated by the target receptor protein. Exemplary transcriptional control sequences are promoter sequences. A reporter gene is meant to include a promoter-reporter gene construct that is heterologously expressed in a cell.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

As used herein, "proliferating" and "proliferation" refer to cells undergoing mitosis.

As used herein, "immortalized cells" refers to cells that have been altered via chemical, genetic, and/or recombinant means such that the cells have the ability to grow through an indefinite number of divisions in culture.

The "growth state" of a cell refers to the rate of proliferation of the cell and the state of differentiation of the cell.

DESCRIPTION OF THE SPECIFIC EMBODIMENTS

Methods and compositions for producing siRNAs, e.g., in the form of a d-siRNA composition, from dsRNAs are provided. In the subject methods, a dsRNA is contacted with a composition that includes an activity that cleaves dsRNA into siRNAs, where the composition efficiently cleaves dsRNA into siRNAs. siRNAs produced by the subject methods find use in a variety of applications, particularly in applications where the specific reduction or silencing of a gene is desired. Also provided are kits for use in practicing the subject invention.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices and materials are now described.

All publications mentioned herein are incorporated herein by reference for the purpose of describing and disclosing the components that are described in the publications which might be used in connection with the presently described invention.

In further describing the subject invention, the subject methods are described first in greater detail, followed by a description of the product d-siRNA compositions produced thereby, a review of various representative applications, including therapeutic applications, in which the subject invention finds use. Finally, kits that find use in practicing the subject invention are discussed.

Methods

As summarized above, the subject invention provides methods of efficiently producing siRNA from dsRNA. More specifically, the subject invention provides methods of producing a plurality of siRNA molecules from a parent dsRNA molecule. By plurality is meant at least 2, usually at least about 5, and more usually at least about 10, where the number of distinct siRNA molecules produced from a given parent dsRNA molecule in the subject methods will often depend on the length of the parent dsRNA molecule, but may be as high as about 25 or higher, e.g., about 100, about 400 or higher. The siRNA product molecules in many embodiments range in length from about 10 to about 30-35 residues, e.g., from about 15 to about 25 residues, including from about 20 to 23 residues, where molecules of 12, 15, 18, 20, 21, 22, 25 and 29 residues in length are of particular interest in certain embodiments.

The length of the parent dsRNA molecules that are employed in the subject methods may vary, but generally the length is at least about 300 bp, usually at least about 500 bp and more usually at least about 1000 bp, where the length may be as long as about 2000 bp or longer, but often does not exceed about 8000 bp, e.g., 6000 bp.

The dsRNA construct may comprise two hybridized strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. The dsRNA construct may be produced enzymatically or by partial-total organic synthesis, any modified ribonucleotide can be introduced by in vitro enzymatic or organic synthesis.

The double-stranded structure may be formed by a single self-complementary RNA strand or two complementary RNA strands. dsRNA constructs containing a nucleotide sequence identical to a portion of a target gene may be employed for inhibition. RNA sequences with insertions, deletions, and single point mutations relative to the target sequence are also of interest for inhibition applications. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene may be of interest. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 50° C. or 70° C. hybridization for 12-16 hours; followed by washing; or conditions that are at least as stringent as these representative conditions). The length of the identical nucleotide sequences may be, for example, at least about 25, about 50, about 100, about 200, about 300 or about 400 bases or longer. In certain embodiments, the dsRNA construct is from about 400 to about 800 bases in length. In certain embodiments, 100% sequence identity between the RNA and the target gene is not required to practice inhibition applications of the invention. Thus the invention has the advantage of being able to tolerate sequence variations that might be expected due to genetic mutation, strain polymorphism, or evolutionary divergence.

The dsRNA construct employed as the parent dsRNA in the present applications may be synthesized either in vivo or in vitro. Endogenous polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the dsRNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. The dsRNA construct may be chemically or enzymatically synthesized by manual or automated reactions. The dsRNA construct may be synthesized by a cellular RNA polymerase or a bacteriophage RNA polymerase (e.g., T3, T7, SP6). The use and production of an expression construct are known in the art (see WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography or a combination thereof. Alternatively, the dsRNA construct may be used with no or a minimum of purification to avoid losses due to sample processing. The dsRNA construct may be dried for storage or dissolved in an aqueous solution. The solution may contain buffers or salts to promote annealing, and/or stabilization of the duplex strands.

In practicing the subject methods, the parent dsRNA molecule as described above, is contacted with a composition enriched for a protein having an activity that cleaves the parent dsRNA substrate into fragments having siRNA activity, i.e., into the desired siRNA population. In other words, the first step of the subject methods is to produce a reaction composition by combining the parent dsRNA and a composition enriched for a protein having an activity that cleaves the parent dsRNA substrate into fragments having siRNA activity.

The dsRNA cleaving protein enriched composition employed in the subject methods is a composition that contains a sufficient amount of an enzyme that cleaves dsRNA into siRNA. In many embodiments, the dsRNA cleaving enzyme present in the composition is a Dicer protein. Dicer is a member of the RNAse III family of nucleases that specifically cleave dsRNA and is evolutionarily conserved in worms, flies, plants, fungi and mammals. The enzyme has a distinctive structure that includes a helicase domain and dual RNAse III motifs. Dicer also contains a region of homology to the RDE1/QDE2/ARGONAUTE family of proteins, which have been genetically linked to RNAi in lower eukaryotes.

Specific Dicer proteins of interest include, but are not limited to:

A) a protein which cleaves dsRNA into siRNA and has an amino acid sequence at least 50 percent identical, and more preferably at least 75, 85, 90 or 95 percent identical to the sequence of human dicer or drosophila dicer (as published in published PCT publication no WO 01/68836 and its counterpart published U.S. Application No. 20020162126, the disclosure of the latter of which is herein incorporated by reference (see sequence id nos 2 and 4 of these publications for the human and mouse sequences, respectively)); and/or which can be encoded by a nucleic acid which hybridizes under wash conditions of 2×SSC at 22° C., and more preferably 0.2×SSC at 65° C., to a nucleic acid (e.g., at least about 25 nt long, such as at least about 50 nt long, including at least about 100 nt long) encoding the above human or drosophila Dicer proteins, (as published in published PCT publication no WO 01/68836 and its counterpart published U.S. Application No. 20020162126, the disclosure of the latter of which is herein incorporated by reference (see sequence id nos 1 and 3 of these publications for the human and mouse sequences, respectively)); the C. elegans dicer (see e.g., NM_060086) and the like.

Additional specific Dicer proteins and nucleic acids encoding the same which are of interest include but are not limited to those having sequences deposited with Genbank and having the following accession nos.: NM_177438; NM_030621; XM_216776.

Also of interest is are bacterial RNAse III proteins that exhibit the desired activity, such as the *E. coli* RNAseIII protein employed in Yang et al., Proc. Nat'l Acad. Sci. USA (Jul. 23, 2002) 99:9942-99947).

Also of interest in the subject methods is the use of homologs of the above specific Dicer proteins, e.g., from other animal species, where such homologs or proteins may be from a variety of different types of species, usually mammals, e.g., rodents, such as mice, rats; domestic animals, e.g. horse, cow, dog, cat; and primates, e.g., monkeys, baboons, humans etc. By homolog is meant a protein having at least about 35%, usually at least about 40% and more usually at least about 60% amino acid sequence identity to the specific human transcription repressor factors as identified above, where sequence identity is determined using the algorithm described supra.

Also of interest are for use in the subject methods are Dicer proteins that are encoded by nucleic acids that are homologous to the above provided nucleic acids, at least with respect to the coding regions thereof. The source of homologous nucleic acids to those specifically listed above may be any mammalian species, e.g., primate species, particularly human; rodents, such as rats and mice, canines, felines, bovines, equines, etc; as well as non-mammalian species, e.g., yeast, nematodes, etc. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al., (1990), *J. Mol. Biol.* 215:403-10 (using default settings, i.e. parameters w=4 and T=17). Unless indicated otherwise, the sequence similarity values reported herein are those determined using the above referenced BLAST program using default settings. Of particular interest in certain embodiments are nucleic acids including a sequence substantially similar to the specific nucleic acids identified above, where by substantially similar is meant having sequence identity to this sequence of at least about 90%, usually at least about 95% and more usually at least about 99%.

Also of interest are nucleic acids that hybridize to the above described nucleic acids under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

In many embodiments, the composition is one that includes recombinant Dicer or an active fragment thereof, i.e., a fragment that retains dsRNA cleaving activity as described above (see e.g., XM_028306 and XM_028307). By recombinant Dicer is meant Dicer that is produced using recombinant nucleic acid protocols.

Recombinant Dicer may be produced using expression vectors containing a nucleic acid encoding a Dicer polypeptide, operably linked to at least one transcriptional regulatory sequence. Operably linked is intended to mean that the nucleotide sequence is linked to a regulatory sequence in a manner that allows expression of the nucleotide sequence. Regulatory sequences are art-recognized and are selected to direct expression of the subject Dicer proteins. Accordingly, the term transcriptional regulatory sequence includes promoters, enhancers and other expression control elements. Such regulatory sequences are described in Goeddel; Gene Expression Technology: Methods hi Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding Dicer polypeptides to recombinantly produce Dicer. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAG or TRC system, T7 promoter whose expression is directed by T7 RNA polymerase, the major operator and promoter regions of phage X, polyhedron promoter, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed.

Moreover, the vector's copy number, the ability to control that copy number and the expression of any other proteins encoded by the vector, such as antibiotic markers, should also be considered.

The recombinant Dicer genes can be produced by ligatng a nucleic acid encoding a Dicer polypeptide into a vector suitable for expression in either prokaryotic cells, eukaryotic cells, or both. Expression vectors for production of recombinant forms of the subject Dicer polypeptides include plasmids and other vectors. For instance, suitable vectors for the expression of a Dicer polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

A number of vectors exist for the expression of recombinant proteins in yeast. For instance, YEP24, YIPS, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a Dicer polypeptide is produced recombinantly utilizing an expression vector generated by sub-cloning the coding sequence of a Dicer gene.

The mammalian expression vectors of certain embodiments contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

As such, the subject proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci. (USA)* (1983) 80:21-25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci. (USA)* (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399, 216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

Once the source of the protein is identified and/or prepared, e.g. a transfected host expressing the protein is prepared, the protein is then purified to produce the desired repressor protein comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express the subject repressor proteins or the expression host expressing the subject repressor proteins, and purified using HPLC, exclusion chromatography, gel electrophoresis, affinity chromatography, and the like.

In many embodiments, the Dicer composition employed in the subject methods is one that is produced recombinantly from a host cell that does not endogenously produce Dicer. As such, the Dicer composition is free of components that are typically associated with Dicer and found in lysates prepared from cells that endogenously produce Dicer. For example, in certain embodiments the Dicer compositions employed in the subject methods are free of the RISC protein and/or the Argonaut protein, where these proteins are known in the art and described in WO 01/68836.

A feature of the subject invention is that the dsRNA cleaving composition employed in the subject methods is not a composition produced by immunoprecipitation protocols, i.e., it is not an IP Dicer preparation. As such, the Dicer preparation employed in the subject methods is one that is free of those components that are typically present in IP produced preparations. Such components which are not present in the Dicer preparations employed in the present invention include: solid phase supports, e.g., beads, as well as other proteins that may be coprecipitated, e.g., that are bound by Dicer or nonspecifically precipitated with Dicer.

In the Dicer compositions employed in the subject invention, the amount of Dicer present in the composition may vary, but is typically at least about 20 ng/µl, usually at least about 40 ng/µl and more usually at least about 160 ng/µl. As such, the composition typically has a Dicer activity, as measured by the assay described in the experimental section, below, of at least about 10% cleavage of large dsRNA, usually at least about 25% cleavage of large dsRNA and more usually at least about 75% cleavage of large dsRNA, where the activity may be as high as about 90% cleavage of dsRNA or higher.

Typically, the composition is an aqueous composition of Dicer, where the composition may include one or more additional components, e.g., buffers, salts like NaCl, $MgCl_2$, EDTA, DTT, ATP and the like.

In certain embodiments, the composition employed includes a single nuclease activity, e.g., DICER. In yet other embodiments, the composition employed includes two or more different activities, e.g., dicer, argonaut, etc.

As summarized above, the first step in the subject methods is to contact the Dicer composition with the substrate dsRNA to produce a reaction composition that is then maintained under conditions sufficient to produce the desired siRNA product. In many embodiments, the subject methods are in vitro methods, by which is meant that they occur in a cell free environment, e.g., not inside of a cell or in the presence of cells. As such, the subject methods are typically performed in a test tube or other analogous in vitro environment. More specifically, the reaction composition produced by combining the substrate parent dsRNA and the cleaving protein enriched composition, as described above, is produced in vitro, i.e., outside of a cell.

The reaction mixture produced by combining the Dicer preparation and the substrate dsRNA typically includes a sufficient amount of $Mg^{2+}$ to ensure adequate Dicer activity, where the amount of $Mg^{2+}$ typically ranges from about 0.5 mM to about 1.0 mM, usually from about 2.5 mM to about 5.0 mM. A feature of the reaction mixtures or compositions in many embodiments of the subject invention is that the reaction mixture is free of ATP, and in other embodiments 1 mM ATP is used.

The reaction mixture is typically maintained under incubation conditions sufficient to produce the desired RNAi product. The reaction mixture is typically maintained at a temperature that ranges from about 30 to about 37° C., usually from about 35 to about 37° C., for a period of time ranging from about 5 hrs to about 10 hrs, usually from about 16 hrs to about 24 hrs. Where desired, the mixture may be agitated/stirred during incubation.

Incubation of the reaction mixture as described above results in the production of a siRNA product. The siRNA product (d-siRNA) is a plurality of distinct siRNA molecules that range in length from about 10 to about 30-35 residues, e.g., from about 15 to about 25 residues, including from about 20 to 23 residues, where molecules of 12, 15, 18, 20, 21, 22, 25 and 29 residues in length are of particular interest in certain embodiments. The number of different or distinct siRNA molecules produced is at least about 2, usually at least about 5, and more usually at least about 10, where the number of distinct siRNA molecules produced from a given parent dsRNA molecule in the subject methods will often depend on the length of the parent dsRNA molecule, but may be as high as about 25 or higher, e.g., about 100, about 400 or higher. In certain embodiments, each distinct siRNA member making up a given d-siRNA product composition ranges in length from about 20-21 to 22 nt, and the number of distinct siRNA members is at least about 25, where this number may be up to and including 100 or more.

The above methods result in the efficient production of a d-siRNA product made up of a plurality of distinct siRNA molecules from a parent dsRNA moelcule. By efficient is meant that at least the majority of the parent substrate dsRNA is cleaved to product siRNA by the subject methods, where the amount of dsRNA that is cleaved is often at least about 60 number %, e.g., at least about 70, 75, 80, 90, 95, etc., number %, as determined using any convenient protocol, e.g., by comparing the amount (e.g., as measured by electrophoresis) of parent dsRNA present in the reaction mixture before and after contact with the Dicer preparation. The siRNA product, i.e., the d-siRNA composition, produced by the subject methods may be used as is or further processed prior to use, e.g., separated from other components of the reaction mixture, e.g., the Dicer protein, other proteins, remaining large dsRNAs, salts, buffers, NTPsetc. Any convenient separation protocol may be employed, including gel purification, chromatographical separation based on molecular weight or affinity resins, and classical preciptiation and the like.

The resultant d-siRNA poducts produced by the methods as described above find use in a variety of different applications, where representative applications are review below.

Utility

The d-siRNA product of the subject methods finds use in a variety of different applications. Representative applications include, but are not limited to: Drug screening/target validation, large scale functional library screening, silencing single genes, silencing families of genes i.e., ser/thr kinases, phosphatases, membrane receptors etc. and the like. The subject d-siRNA products also find use in therapeutic applications, as described in greater detail separately below.

One representative utility of the present invention is as a method of identifying gene function in an organism, especially higher eukaryotes comprising the use of the product d-siRNA to inhibit the activity of a target gene of previously unknown function. Instead of the time consuming and laborious isolation of mutants by traditional genetic screening, functional genomics using the subject product d-siRNA determines the function of uncharacterized genes by employing the d-siRNA to reduce the amount and/or alter the timing of target gene activity. The product d-siRNA can be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for mammalian genomes, can be coupled with use of the product d-siRNA to determine gene function in a cell or in a whole organism. The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects.

A simple representative assay inhibits gene expression according to the partial sequence available from an expressed sequence tag (EST). Functional alterations in growth, development, metabolism, disease resistance, or other biological processes would be indicative of the normal role of the ESTs gene product.

The ease with which the product d-siRNA construct can be introduced into an intact cell/organism containing the target gene allows the present invention to be used in high throughput screening (HTS). For example, individual clones from the library can be replicated and then isolated in separate reactions, but preferably the library is maintained in individual reaction vessels (e.g., a 96 well microtiter plate) to minimize the number of steps required to practice the invention and to allow automation of the process. Solutions containing the product d-si RNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity.

The d-siRNA can be fed directly to, injected into, the cell/organism containing the target gene. The d-siRNA construct may be directly introduced into the cell (i.e., intracellularly); or introduced extracellularly into a cavity, interstitial space, into the circulation of an organism, introduced orally, or may be introduced by bathing an organism in a solution containing the d-siRNA. Methods for oral introduction include direct mixing of RNA with food of the organism. Physical methods of introducing nucleic, acids include injection directly into the cell or extracellular injection into the organism of an RNA solution. The d-siRNA may be introduced in an amount which allows delivery of at least one copy per cell. Higher doses (e.g., at least 5, 10, 100, 500 or 1000 copies per cell) of d-siRNA material may yield more effective inhibition; lower doses may also be useful for specific applications. Inhibition is sequence-specific in that nucleotide sequences corresponding to the duplex region of the RNA are targeted for genetic inhibition.

The function of the target gene can be assayed from the effects it has on the cell/organism when gene activity is inhibited. This screening could be amenable to small subjects that can be processed in large number, for example, tissue culture cells derived from invertebrates or invertebrates, mammals, especially primates, and most preferably humans.

If a characteristic of an organism is determined to be genetically linked to a polymorphism through RFLP or QTL analysis, the present invention can be used to gain insight regarding whether that genetic polymorphism might be directly responsible for the characteristic. For example, a fragment defining the genetic polymorphism or sequences in the vicinity of such a genetic polymorphism can be amplified to produce a dsRNA from which d-siRNA is prepared according to the subject methods, which d-siRNA can be introduced to the organism or cell, and whether an alteration in the characteristic is correlated with inhibition can be determined.

The present invention is useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of d-siRNA at specific times of development and locations in the organism without introducing permanent mutations into the target genome.

In situations where alternative splicing produces a family of transcripts that are distinguished by usage of characteristic exons, the present invention can target inhibition through the appropriate exons to specifically inhibit or to distinguish among the functions of family members. For example, a hormone that contained an alternatively spliced transmembrane domain may be expressed in both membrane bound and secreted forms. Instead of isolating a nonsense mutation that terminates translation before the transmembrane domain, the functional consequences of having only secreted hormone can be determined according to the invention by targeting the exon containing the transmembrane domain and thereby inhibiting expression of membrane-bound hormone.

Therapeutic Applications

The subject d-siRNA compositions produced by the subject methods also find use in a variety of therapeutic applications in which it is desired to selectively modulate, e.g., one or more target genes in a host, e.g., whole mammal, or portion thereof, e.g., tissue, organ, etc, as well as in cells present therein. In such methods, an effective amount of a d-siRNA composition is administered to the host or target portion thereof. By effective amount is meant a dosage sufficient to selectively modulate expression of the target gene(s), as desired. As indicated above, in many embodiments of this type of application, the subject methods are employed to reduce/inhibit expression of one or more target genes in the host or portion thereof in order to achieve a desired therapeutic outcome.

Depending on the nature of the condition being treated, the target gene may be a gene derived from the cell, an endogenous gene, a pathologically mutated gene, e.g. a cancer causing gene, one or more genes whose expression causes or is related to heart disease, lung disease, alzheimer's disease, parkinson's disease, diabetes, arthritis, etc.; a transgene, or a gene of a pathogen which is present in the cell after infection thereof, e.g., a viral (e.g., HIV-Human Immunodeficiency Virus; HBV-Hepatitis B virus; HCV-Hepatitis C virus; Herpes-simplex 1 and 2; Varicella Zoster (Chicken pox and Shingles); Rhinovirus (common cold and flu); any other viral form) or bacterial pathogen. Depending on the particular target gene and the dose of d-siRNA delivered, the procedure may provide partial or complete loss of function for the target gene. Lower doses of injected material and longer times after administration of d-siRNA may result in inhibition in a smaller fraction of cells.

The subject methods find use in the treatment of a variety of different conditions in which the modulation of target gene expression in a mammalian host is desired. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The present invention is not limited to modulation of expression of any specific type of target gene or nucleotide sequence. Representative classes of target genes of interest include but are not limited to: developmental genes (e.g., adhesion molecules, cyclin kinase inhibitors, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, EBRB2, ETSI, ETS1, ETV6, FOR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES); tumor suppressor genes (e.g., APC, BRCA 1, BRCA2, MADH4, MCC, NF 1, NF2, RB 1, TP53, and WTI); and enzymes (e.g., ACC synthases and oxidases, ACP desaturases and hydroxylases, ADPglucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, Upases, lipoxygenases, lysolymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); chemokines (e.g. CXCR4, CCR5), the RNA component of telomerase, vascular endothelial growth factor (VEGF), VEGF receptor, tumor necrosis factors nuclear factor kappa B, transcription factors, cell adhesion molecules, Insulin-like growth factor, transforming growth factor beta family members, cell surface receptors, RNA binding proteins (e.g. small nucleolar RNAs, RNA transport factors), translation factors, telomerase reverse transcriptase); etc.

As indicated above, the d-siRNA can be introduced into the target cell(s) using any convenient protocol, where the protocol will vary depending on whether the target cells are in vitro or in vivo.

Where the target cells are in vivo, the d-siRNA can be administered to the host comprising the cells using any convenient protocol, where the protocol employed is typically a nucleic acid administration protocol, where a number of different such protocols are known in the art. The following discussion provides a review of representative nucleic acid administration protocols that may be employed. The nucleic acids may be introduced into tissues or host cells by any number of routes, including microinjection, or fusion of vesicles. Jet injection may also be used for intra-muscular administration, as described by Furth et al. (1992), *Anal Bio-*

*chem* 205:365-368. The nucleic acids may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

For example, the d-siRNA agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. Patents of interest include U.S. Pat. Nos. 5,985,847 and 5,922,687 (the disclosures of which are herein incorporated by reference); WO/11092;. Acsadi et al., New Biol. (1991) 3:71-81; Hickman et al., Hum. Gen. Ther. (1994) 5:1477-1483; and Wolff et al., Science (1990) 247: 1465-1468; etc.

Depending n the nature of the d-siRNA, the active agent(s) may be administered to the host using any convenient means capable of resulting in the desired modulation of target gene expression. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

Kits

Also provided are reagents and kits thereof for practicing one or more of the above-described methods. The subject reagents and kits thereof may vary greatly. Typically, the kits at least include a Dicer preparation, as described above. The subject kits may also include one or more additional reagents, e.g., reagents employed in generating dsRNA as described above, dsRNA, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which

EXPERIMENTAL

I. Materials and Methods

A. Dicer Expression and Purification.

The coding region of human Dicer (Acc. No. NM 030621) with N-terminal $His_6$- and T7-epitope tags was expressed in Hi5 cells (Invitrogen-BTI-TN-5B1-4) using the Bac-to-Bac expression system (Gibco-pFastbac-HTC). After 48 hrs of expression, cell pellets were either stored at −80° C. or lysed in extraction buffer (300 mM NaCl, 50 mM $NaPO_4$, 1% NP-40, pH 8.0) by sonication. Cellular debris and insoluble proteins were removed by centrifugation at 10,000 g. r-Dicer was affinity purified in batch from the total soluble protein using Talon™ resin (Clontech) as recommended by manufacturer. Briefly, r-Dicer was bound to Talon™ resin at 4° C. for 1 hr, washed twice (500 mM NaCl, 50 mM $NaPO_4$, 1% NP-40, pH 8.0), washed a third time (500 mM NaCl, 50 mM $NaPO_4$, pH 8.0), and eluted (500 mM NaCl, 50 mM $NaPO_4$, 150 mM imidazole, pH 8.0). Further purification of r-Dicer using HiTrap Q HP (Amersham) was done according to manufacturer with a linear elution gradient (Buffer A: 25 mM NaCl, 50 mM $NaPO_4$, pH 8.0; Buffer B: 1 M NaCl, 50 mM $NaPO_4$, pH 8.0). Slide-A-Lyzers (Pierce) were used for dialysis as recommended by manufacturer (500 mM NaCl, 60 mM HEPES, 0.1 mM EDTA, pH 8.0). Samples were electrophoresed on 6% (100:1) polyacrylamide gels and were either Coomassie-stained or transferred to PVDF (Amersham). The mouse α-T7-HRP antibody (Novagen) was used for western blotting as directed by manufacturer (1:5000).

B. RNA Preparation.

Large dsRNAs (~500 bp) were made by annealing single stranded RNAs that were in vitro transcribed from SP6 and T7 promoter sequences at either end of a template generated by PCR. (Alterntively, T7 promoter sequences can be employed at both ends to obviate a separate annealing step). Annealing was carried out by heating sense and antisense RNA (3 µM each) at 95° C. for 1 min and then incubating overnight at room temperature in 20 mM NaCl, 10 mM HEPES pH 8.0. Chemically synthesized siRNAs were synthesized by Pharmacon and were deprotected and provided by Greg Hannon (Cold Spring Harbor Laboratory), as previously described (Elbashir, S. M., et al., Genes Dev. 15,188-200. (2001)). The accession numbers and regions targeted are as follows and correspond to the region relative to the start codon. For GL3 (Acc. No. U47296), the chemically synthesized siRNA targeted 153-173 and the d-siRNAs targeted 113-614. For RL (Acc. No. AF025846) the d-siRNAs targeted the 118-618 region. For GFP (Acc. No. U55761), the chemically synthesized siRNA targeted 83-103 and the d-siRNAs targeted 69-568. For VegT (Acc. No. U59483) the d-siRNAs targeted 733-1377.

C. In Vitro Dicing.

For analysis of r-Dicer activity, typically 500 ng of dsRNA (500 bp) was combined with lysate or a column fraction that did or did not contain r-Dicer (reaction contained: 250 mM NaCl, 30 mM HEPES, 0.05 mM EDTA, 1 mM ATP, 2.5 mM $MgCl_2$, pH 8.0 where half of the volume consisted of lysate or column fraction) and incubated for 12-16 hrs at 37° C. For some of the reactions shown in FIG. 1C, these standard conditions were modified by including 20 U of RNasin (Promega), by leaving out $Mg^{2+}$ and/or ATP, or by substituting 500 ng of ssRNA or dsDNA for the dsRNA. Reaction was quenched with the addition of 10 mM EDTA, treated with proteinase K (0.2 mg/ml), phenol-chloroform-isoamyl alcohol extracted, and electrophoresed in a 15% polyacrylamide native gel (29: 1 acrylamide:bisacrylamide).

Gel was cast in 1×TBE, pH 8.5 and electrophoresed in 0.5×TBE pH 8.5 at 4° C. For production of d-siRNAs typically 5 µg of dsRNA was incubated with r-Dicer (same reaction conditions as above but r-Dicer comprised only 10% of reaction volume). Reaction was quenched with 10 mM EDTA, desalted using G-25 spin column (Amersham), deproteinated using EZ-pure (Millipore), and any remaining large dsRNA was removed using Micron-100 (Millipore). Electrophoresis in a 15% acrylamide native gel (as described above) was carried out to verify that the d-siRNAs were not contaminated with large dsRNAs.

To determine the precise size of d-siRNAs (FIG. 2A), $^{32}$P-labeled RNA was electrophoresed on an 18% (wt/vol) denaturing polyacrylamide sequencing gel. Size standards were generated by alkaline hydrolysis of $^{32}$P-labeled single stranded Xenopus β-actin mRNA. For more routine analyses, d-siRNAs were electrophoresed on a 15% (wt/vol) polyacrylamide gel with a synthetic 21 bp siRNA as a size standard.

D. 5'-Phosphorylation of d-siRNAs. A synthetic siRNA (GL3) and various d-siRNAs (15 pmol) were incubated at 37° for 1 h in shrimp alkaline phosphatase (SAP) buffer (USB) in the presence or absence of 15 U SAP (USB). SAP was inactivated by heating at 65° C. for 15 minutes in the presence of 10 mM EDTA. The siRNA and d-siRNAs were subsequently incubated with 10 U T4 polynucleotide kinase (New England Biolabs) and 10 µCi [γ-$^{32}$P]ATP (Amersham). Reaction products were analyzed by 15% (wt/vol) native PAGE followed by ethidium bromide staining and phosphorimaging.

E. Cell Culture and Transfections.

The bacmid encoding r-Dicer was generated by recombination in DH10Bac cells (Invitrogen). Virus encoding r-Dicer was generated (by transfection of bacmid with cellFECTIN, Invitrogen) and amplified in Sf9 cells (Invitrogen-IPLB-SF-21-AE) as directed by manufacturer. Hi5 cells (Invitrogen-BTI-TN-5B1-4) were grown and infected as instructed by manufacturer (Invitrogen).

293 and RBL cells were grown at 37° C., in 10% $CO_2$, and in Dulbecco's modified Eagle's medium (D-MEM) supplemented with 10% FBS, 100 units/ml penicillin, and 100 µg/ml streptomycin. 24 hours before transfection, cells were plated onto 24 well plates at 90% confluence in D-MEM supplemented with 10% FBS, without antibiotics. Co-transfections of 1 µg pGL3-SV40 (Promega), 5 ng pRL-CMV (Promega), and either 210 ng d-siRNAs or 210 ng chemically synthesized siRNAs were carried out in 24 well plates using Lipofectamine 2000 (Invitrogen) as described by the manufacturer. Cells were lysed 20 hours post transfection and analyzed for luciferase activity (Dual-luciferase kit, promega).

For silencing endogenous genes, HEK 293 cells were transferred into 12-well plates at 50% confluence the day before transfection. d-siRNAs were transfected using Genesilencer reagent (Gene Therapy Systems, San Diego). Cells were lysed 72 hours post-transfection by vortexing in cold lysis buffer (0.42 M NaCl, 100 mM Tris pH 7.9, 0.5% Triton X-100, 1 mM EDTA, 1 mM EGTA) supplemented with protease inhibitors (aprotonin 1 µg/ml, 0.2 mM PMSF, pepstatin, leupeptin, and chymostatin all at 0.2 µg/ml). Lysates (~60 µg protein) were subjected to SDS-PAGE and transferred to PVDF (Amersham). Blots were probed with various antibodies: actin (1:200, Santa Cruz), Cdc25A (1:500, Santa Cruz), Cdc25C (1:500, Santa Cruz), cyclin E1 (1:500, Santa Cruz) or phospho-eIF2α (1:500, Biosource International). Secondary antibodies were conjugated to either alkaline phosphatase (AP; Sigma) or horseradish peroxidase (HRP; Amersham) and used at 1:2500. The Immun-Star HRP chemiluminescent detection kit (Bio-Rad) was used for HRP detection and CDP-Star (Tropix-Perkin Elmer) for AP.

F. Activity Assay 293 cells were transfected with a plasmid encoding Dicer with two N-terminal tags, $His_6$ and the T7 epitope or an irrelevant plasmid as a negative control. After 3 days of expression cells were lysed in immunoprecipitation buffer. Dicer was immunoprecipitated with a T7 antibody. The agarose-antibody conjugate was then incubated with 40 pmol of internally labeled 500 bp dsRNA for 2.5 hr in normal reaction conditions. Various amounts of r-Dicer (1, 2.5, 5, 10, 15 µl) were also incubated with 40 pmol of internally labeled 500 bp dsRNA under the same conditions. The RNA was then electrophoresed in a 15% native polyacrylamide gel. The amount of d-siRNA produced was then determined by phosphorimaging. To determine the specific activity the amount of protein that cleaves a percentage of dsRNA is measured. Protein amount is measured by western blotting.

II. Results Full-length, $His_6$— and T7-tagged-Dicer was expressed in Hi5 insect cells by baculovirus infection and purified on a cobalt Sepharose column. The main protein eluted was a 225 kDa protein, which corresponds to the predicted molecular mass for Dicer (FIG. 1A, top panel, left side). The 225 kDa band co-migrated with the main immunoreactive band on an anti-tag immunoblot, confirming its identity as recombinant Dicer (FIG. 1A, middle panel, left side).

Figures 2A, 2B, 2C, 2D, 2E, 2F, 2G, 2H:
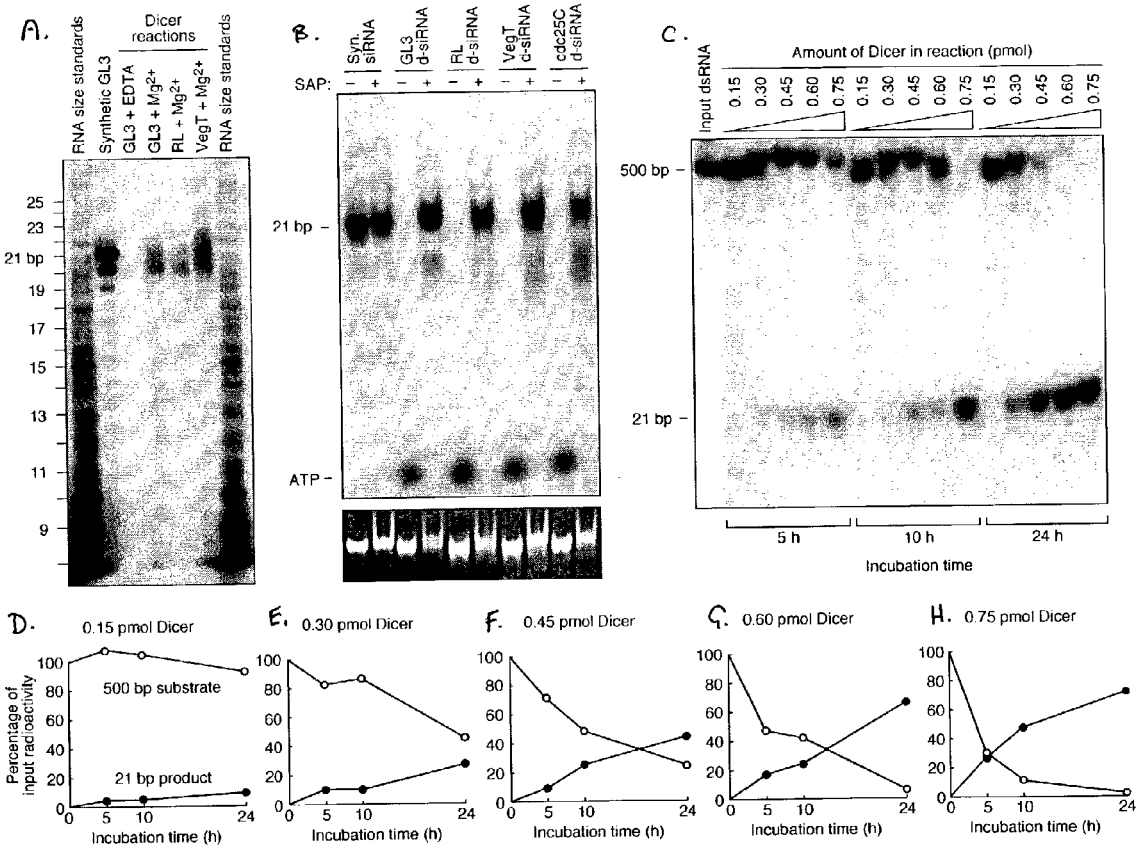
FIGS. 2A to H. Production of pools of siRNAs by purified recombinant Dicer. (A) The size of d-siRNAs produced by r-Dicer. Three different ~500 bp dsRNAs were incubated with r-Dicer. The reactions were then electrophoresed on an 18% sequencing gel. The radiolabeled siRNA and d-siRNAs were visualized by exposure to a phosphorimager and the size of the d-siRNAs were determined by comparison to a synthetic 21 bp siRNA and to a single base pair ladder. (B) Phosphorylation status of the 5'-end of various d-siRNAs. A synthetic siRNA or various d-siRNAs were incubated in shrimp alkaline phosphatase (SAP) buffer either in the presence or absence of SAP, followed by T4 polynucleotide kinase and [$\gamma$-$^{32}$P]ATP. Reactions were electrophoresed on a 15% native polyacrylamide gel. The amount of radioactivity present was visualized using a phosphorimager (upper panel) and the presence of the siRNA or d-siRNA was confirmed by staining with ethidium bromide (lower panel). (C-H) Analysis of the efficiency with which r-Dicer cleaves the ~500 bp dsRNA substrate into 20-21 bp d-siRNA products. Increasing amounts of r-Dicer were incubated with a constant amount (1 µg) of the ~500 bp substrate. The reactions were stopped at 5, 10 and 24 hours. Substrate and products were separated on a 15% native polyacrylamide gel and then visualized (C) and quantified (D-H) with a Phosphorimager.

It was then determined that the purified recombinant Dicer was able to process dsRNA into siRNAs. We incubated samples with a 500 bp dsRNA, submitted the reaction products to native polyacrylamide gel electrophoresis, and looked for the production of ~22 bp products. The purified Dicer efficiently converted the dsRNA to 20-21-22 bp forms (FIG. 1A, bottom panel, left side; FIG. 2A).

Because Drosophila extracts are capable of generating siRNAs, it is likely that the Hi5 insect cells used to produce r-Dicer contained some endogenous Dicer activity. Therefore, we addressed the question of whether the Dicer activity in our purified fractions was due to the r-Dicer or to some co-purifying insect protein. We subjected lysates from uninfected Hi5 cells to the same purification procedure and assessed fractions for Dicer activity. A small amount of RNA processing activity could be detected in the total soluble Hi5 cell lysate and in the flow through from the cobalt affinity column (FIG. 1A, bottom panel, right side). However this activity was not detected in the column eluates, indicating that it could not account for the high levels of Dicer activity seen in the purified r-Dicer preparation. These data indicate that the r-Dicer is responsible for the Dicer activity seen in the purified fractions.

Figure 1B:
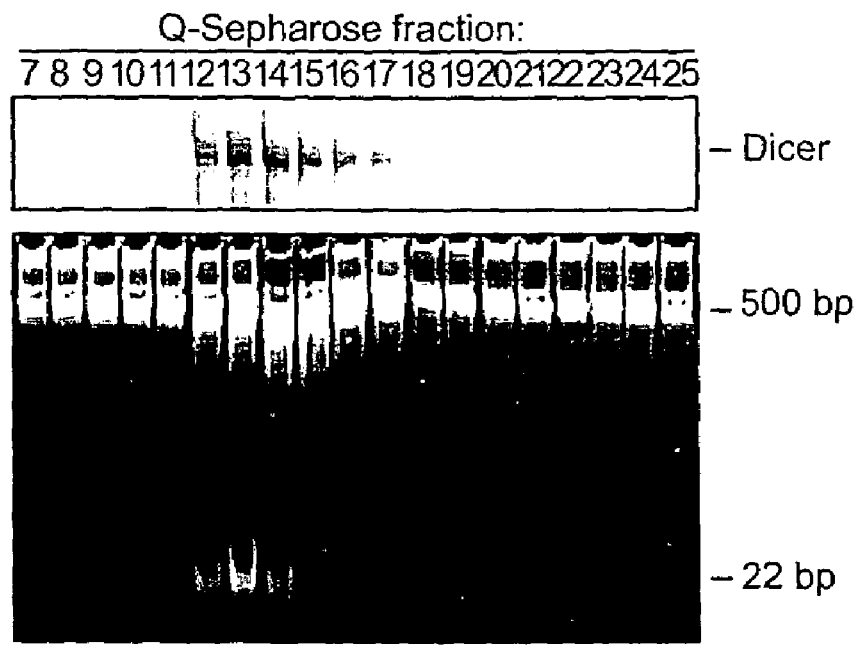
Figure 1C:
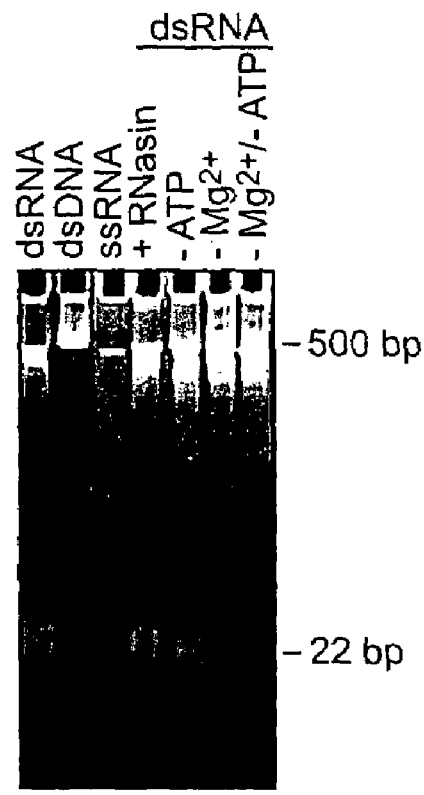

Previous in vitro data demonstrated that Dicer is capable of interacting with other proteins implicated in RNA interference. Thus, it seemed plausible that active r-Dicer might be a complex consisting of r-Dicer and some endogenous insect cell proteins. Since the r-Dicer is highly overexpressed in the Hi5 cells, this putative complex would likely account for a small proportion of the total expressed r-Dicer, and so the bulk of the r-Dicer protein might be chromatographically separable from the active r-Dicer. We therefore subjected the purified, active r-Dicer to Q-Sepharose ion exchange chromatography and assessed whether or not the r-Dicer protein and Dicer activity co-eluted. As shown in FIG. 1B, the protein and activity did co-elute. Thus, there is no evidence that r-Dicer requires other proteins for activity.

r-Dicer was subjected to various reaction conditions to determine cofactor and substrate specificity as well as to ensure that the 20-21-mers were generated by r-Dicer and not a nonspecific RNase or nuclease. dsRNA was efficiently processed by r-Dicer (FIG. 1C, lane 1) but dsDNA was not (FIG. 1C, lane 2), establishing that r-Dicer is RNA-specific. r-Dicer generated small amounts of 22 bp product from ssRNA, which may be due to cleavage of hairpins or contaminating dsRNA (FIG. 1C, lane 3, and data not shown). r-Dicer was not inhibited by RNasin (FIG. 1C, lane 4), distinguishing it from most ribonucleases. $Mg^{2+}$ was required for r-Dicer activity (FIG. 1C, lanes 6 and 7), but ATP was not (FIG. 1C, lane 5). In contrast, other workers have found that ATP is important for RNAi and dicing in extracts and in Dicer immunoprecipitates (Zamore, et al., Cell 101, 25-33. (2000); Bernstein, et al., Nature 409, 363-366. (2001).; Nykanen, et al., Cell 107, 309-321. (2001)). The reason for this difference is unclear, but it is possible that ATP is more important for the activity of crude Dicer preparations than it is for purified Dicer preparations. High concentrations of manganese (2.5-5 mM) and calcium (10 mM) inhibited r-Dicer activity (data not shown). siRNAs produced in Drosophila extracts are 5'-phosphorylated, and this is important for gene silencing (Elbashir, S.M., Lendeckel, W. & Tushcl, T. RNA interference is mediated by 20-, 21- and 22-nucleotide RNAs. *Genes Dev* 15, 188-200. (2001)). To determine if d-siRNAs are 5'-phosphorylated, d-siRNAs were incubated with or without shrimp alkaline phosphatase (SAP), followed by T4 polynucleotide kinase and [γ-32P]ATP. SAP-dephosphorylated d-siRNAs were phosphorylated by T4 polynucleotide kinase, but mock-dephosphorylated d-siRNAs were not (FIG. 2B), indicating that d-siRNAs are quantitatively monophosphorylated at their 5'-ends. A synthetic siRNA, which has a 5'-hydroxyl group rather than a 5'-phosphate, was phosphorylated by T4 polynucleotide kinase with or without SAP treatment (FIG. 2B).

To explore the mechanism of in vitro dicing and determine whether useful amounts of d-siRNAs could be produced, we quantified d-siRNA production as a function of time and Dicer concentration (FIGS. 2C—H). Substantial yields were obtained; at the highest Dicer concentration used (75 nM), ~70% of the starting material was converted to d-siRNAs within 24 h (FIG. 2C, H). The amount of product produced (50 pmol) greatly exceeded the amount of Dicer used (0.75 pmol) (FIG. 2C, H), indicating that processing was enzymatic rather than stoichiometric. The high yields also imply that r-Dicer must produce a complex pool of 20-21 bp products rather than one or two predominant products. dsRNAs intermediate between the 500 bp substrate and 20-21 bp product were not detected (FIG. 2C), suggesting that r-Dicer cleaves dsRNA processively.

We next assessed whether d-siRNAs were capable of specific gene silencing. d-siRNAs and siRNAs (FIG. 3A) were co-transfected with firefly and Renilla luciferase constructs into HEK 293 cells, and after 20 h of expression, firefly (FIG. 3B) and Renilla (FIG. 3C) luciferase activities were assayed individually (Elbashir, S. M. et al. Duplexes of 21-nucleotide RNAs mediate RNA interference in cultured mammalian cells. Nature 411, 494-498. (2001)). Diced GL3 siRNAs were found to be comparable to a highly effective synthetic siRNA in inhibiting firefly luciferase expression, and control siRNAs (a synthetic GFP siRNA and VegT and RL d-siRNAs) had no effect (FIG. 3B). RL d-siRNAs inhibited Renilla luciferase expression, and again the control GFP siRNA and VegT d-siRNAs had no effect (FIG. 3C). GL3 d-siRNAs caused some inhibition of Renilla luciferase expression (FIG. 3C; see also FIG. 3F for a second set of experiments). This may represent an off-target effect; however, as noted above, RL d-siRNAs had no effect on firefly luciferase expression, so off-target effects are not an inevitable consequence of using d-siRNAs (also note that VegT (FIG. 3B,C) and GFP (FIG. 3E,F) d-siRNAs do not affect either form of luciferase at lower concentrations). Both the synthetic and diced GL3 siRNAs shifted the ratio of firefly-to-Renilla luciferase expression toward Renilla luciferase, with the synthetic GL3 siRNA being somewhat more selective than the diced GL siRNA, and the RL d-siRNAs shifted the ratio towards firefly luciferase (FIG. 3D). Thus, both of the d-siRNAs were selective for the correct species.

Concentrations of synthetic siRNAs as low as 1.5 nM are sometimes capable of specific gene silencing (Elbashir, S. M. et al. Duplexes of 21-nucleotide RNAs mediate RNA interference in cultured mammalian cells. Nature 411, 494-498. (2001)). However, many synthetic siRNAs are less effective, and so it was of interest to see how d-siRNA pools compared to a highly effective siRNA in potency. To ensure silencing observed with d-siRNAs was not due to contaminating large dsRNA left over after M-100 chromotography, d-siRNAs were also gel purified, and the two distinct preps were compared. As shown in FIG. 3E (dark gray bars), the synthetic and diced GL3 siRNAs all decreased firefly luciferase expression by about 90% at the lowest concentration (3 nM) tested, and showed greater silencing at higher concentrations. Thus, the potency of the GL3 d-siRNA pools compared well to that of the synthetic GL3 siRNA. Gel-purified and M-100-purified d-siRNAs were similar to each other in efficacy, suggesting that effective gene silencing is not affected by purification strategy (FIG. 3E).

We compared the non-specific effects of diced and synthetic siRNAs by examining the effect of GFP siRNAs on the expression of firefly and Renilla luciferases. Neither the synthetic nor the diced GFP siRNAs (gel purified or M-100 purified) significantly inhibited GL3 luciferase (FIG. 3E) or Renilla luciferase (FIG. 3F) expression at concentrations below 30 nM. At higher concentrations, all three GFP siRNA preparations non-specifically silenced both luciferases, with the synthetic GFP siRNA causing the least silencing and the gel-purified GFP d-siRNA the most (FIG. 3E, F). Thus, the siRNA and d-siRNAs had similar concentration windows for specific gene silencing, and none was free of non-specific effects at concentrations of 100 nM and greater. Some of the non-specific silencing was probably due to an interferon response, as indicated by elevated levels of eIF2a phosphorylation (Stark, G. R., Kerr, I. M., Williams, B. R., Silverman, R.H. & Schreiber, R. D. How cells respond to interferons. Annu Rev Biochem 67, 227-264. (1998)) (e.g. FIG. 3H, the 100 and 300 nM M-100 d-GFP samples). However, some samples showed little elevation of eIF2α phosphorylation, but still showed a non-specific decrease in luciferase expression (e.g. FIG. 3H, the 100 and 300 nM gel-purified d-GFP samples), indicating that mechanisms other than the interferon response contributed to the decreased luciferase expression. Gel-purified and M-100-purified d-siRNAs were generally similar in toxicity (FIGS. 3E-G), although increases in eIF2α phosphorylation were seen with some of the M-100-purified d-siRNAs, but not with gel purified d-siRNAs (FIG. 3H). The diced and synthetic GL3 siRNAs all showed selectivity for firefly luciferase over Renilla luciferase at both low and high siRNA concentrations (FIG. 3G, dark gray bars).

Next we assessed whether d-siRNAs can inhibit the expression of endogenous genes. The first target examined was cyclin E1, the regulatory subunit of the Cdk2/cyclin E1 complex. HEK 293 cells were transfected with two concentrations of cyclin E1 d-siRNAs, an irrelevant control d-siRNA (RL luciferase), or water, and the amount of endogenous cyclin E1 protein remaining after 72 hours was assessed. As shown in FIG. 4A, 30 nM d-siRNAs caused some decrease in cyclin E1 levels, and 60 nM d-siRNA largely eliminated the cyclin E1 protein. Little eIF2α phosphorylation was seen in cells treated with cyclin E1 d-siRNAs (FIG. 4A). A higher level of eIF2α phosphorylation was seen in cells treated with RL d-siRNAs (FIG. 4A), probably due to the persistence of the RL d-siRNAs in cells that do not possess an RL luciferase target. Nevertheless, even this extent of eIF2α phosphorylation did not result in a detectable decrease in cyclin E1 protein levels (FIG. 4A), indicating that an interferon response could not account for the decreased cyclin E1 levels seen in cyclin E1 d-siRNA-treated cells.

As a second target we examined Cdc25C. Cdc25C is one of three closely-related phosphatases (Cdc25A, B, and C) that dephosphorylate and activate cyclin-dependent kinases, allowing us to address the question of off-target gene silencing again in a more natural context. dsRNAs corresponding to the entire coding regions of Cdc25C were diced in vitro. The d-siRNAs were gel purified and transfected into HEK 293 cells, and the expression of Cdc25C and Cdc25A was assessed by immunoblotting. The Cdc25C d-siRNAs decreased Cdc25C by about 90%, without increasing eIF2α phosphorylation (FIG. 4B). Expression of Cdc25A was unaffected (FIG. 4B), even though Cdc25C and Cdc25A share stretches of 13-15 consecutive identical nucleotides and several longer stretches with single mismatches. d-siRNAs derived from an irrelevant B-Raf cDNA had no effect on either Cdc25C or Cdc25A expression (FIG. 4B). Thus Cdc25C d-siRNAs specifically silenced the expression of Cdc25C.

In summary, r-Dicer processes large dsRNAs into 20-21 bp siRNAs suitable for gene silencing studies in mammalian cells. Yields are high, up to 70%, and the products of the Dicer reaction are easily purified away from any residual large dsRNA by M-100 chromatography or gel purification. Diced siRNAs are comparable in potency to synthetic siRNAs, and are similar in terms of non-specific toxicity as well. For some purposes (e.g. knockdowns of splice variants, stable knockdowns, or conditional knockdowns), individual siRNAs may still be preferable to d-siRNAs. However, for general functional studies, d-siRNAs are simple to produce, effective in gene silencing, and easily scalable, making them a useful addition to the siRNA arsenal.

III. Representative In vitro Dicing-Single Gene Silencing Protocol

The following representative protocol describes a way to specifically silence a single gene in cell culture according to the subject invention. The following protocol is based on the previous finding that small interfering RNAs (siRNAs) induce gene silencing in cultured cells (Elbashir, et al., supra) and an RNase III family enzyme, Dicer, is capable of cleaving larger dsRNAs into 22-mers (Bernstein, et al., Nature 409, 363-366. (2001)). Purified recombinant Dicer (r-Dicer) is used to cleave larger dsRNAs into d-siRNAs. The general strategy is to pick a region in Your Favorite Gene (YFG), make a template for generating large dsRNA in vitro, incubate dsRNA with r-Dicer, purify d-siRNAs, and introduce into cells.

A. r-Dicer Purification r-Dicer is produced by infection of Hi5 cells with baculovirus and is subsequently purified, in batch, using cobalt resin.

1. Infect Hi5 cells with 100 μl of virus per $1\times10^7$ cells and express for 46-48 hours. Pellets can be directly subjected to purification or stored at −80° C. Typically $1\times10^8$ cells are infected with 1 ml of virus. Protein production is efficient in either adherent or suspension cultures.
2. Pellets ($1\times10^8$ cells) are resuspended in 10 ml of α-extraction buffer. Add protease inhibitors to a final concentration of: 1 mM PMSF: 0.55 μg/ml leupeptin; 0.55 μg/ml pepstatin; 1 μg/ml aprotonin

| α-pH 8.0 | |
|---|---|
| 50 mM | NaPO₄ |
| 300 mM | NaCl |
| 1% | NP-40 |

3. Cells are lysed by sonication, 5×10 second pulses at 40% duty cycle, in an ice slurry. Allowing samples to chill for 30 seconds between the 10-second pulses prevents heating of the sample.
4. Cell debris and insoluble proteins are removed by centrifugation at 10,000×g for 20 minutes at 4° C. About 50% of r-Dicer is present in the soluble fraction
5. The 10,000×g supernatant is mixed (using a conventional rotator) with a 500 μl bed volume of cobalt Sepharose (Talon, Clontech; capacity 3 mg/1 ml bed volume) for 1 hour at 4° C. to allow binding of r-Dicer to the resin. Note: the resin is washed twice with 20 volumes of α-extraction buffer; resin is collected by centrifugation at 700×g.
6. After binding, the resin is again collected by centrifugation at 700×g and 4° C. for 5 minutes.
8. Resin is washed twice by mixing for 10 minutes at 4° C. with 20 volumes of β-wash buffer. Resin is collected by centrifugation at 700×g and 40 C for 2 minutes.

| β-pH 8.0 | |
|---|---|
| 50 mM | NaPO₄ |
| 500 mM | NaCl |
| 1% | NP-40 |

8. 2 additional washes with β -minus buffer are used to remove the detergent (NP-40). Washes are performed as in step 7.

| β-pH 8.0 | |
|---|---|
| 50 mM | NaPO₄ |
| 500 mM | NaCl |

9. r-Dicer is eluted by five successive elutions with 500 μl of γ-elution buffer. Between elutions resin is collected by centrifugation at 700×g and 40 C for 2 minutes.

| γ-pH 8.0 | |
|---|---|
| 50 mM | NaPO₄ |
| 500 mM | NaCl |
| 150 mM | imidazole |

10. The elution fractions are dialyzed (Slide-A-lyzer, Pierce) at 4° C. against 3 L of dialysis buffer. Three successive 1 L dialyses are performed, the first two for two hours and the third overnight. r-Dicer is stored at 4° C.

| Dialysis-pH 8.0 | |
|---|---|
| 60 mM | Hepes pH 8.0 |
| 500 mM | NaCl |
| 0.1 mM | imidazole |

11. The 225 kDa r-Dicer can be detected by Coomassie-staining or Western blotting (anti-T7 or anti-His) after electrophoresis in a 6%, 100:1 SDS-polyacrylamide gel.

To obtain higher protein yields, the above protocol can be modified to start with more material, e.g., $4\times10^8$ cells.

B. Activity Assay 1. r-Dicer activity can be assayed by setting up a Dicer reaction. About 80% of the large dsRNA will be cleaved into d-siRNAs when the following reaction conditions are used.

Reaction Conditions

| | |
|---|---|
| X μl | dsRNA (500 ng) |
| 1.0 μl | 10 mM ATP* |
| 0.5 μl | 50 mM MgCl₂ |
| 4.0 μl | Rxn Dil. Bfr.* |
| 1.0 μl | Enzyme |
| X μl | H₂O |
| 10.0 μl | |

*pH 8.0; Incubate @ 37° C. 18-22 hours

2. After overnight incubation the reaction is quenched with EDTA to a final concentration of 10 mM and extracted with phenol-chloroform-isoamyl alcohol (25:24:1). The RNA is then electrophoresed in a 15% native polyacrylamide gel (29:1, cast in 1× and electrophoresed in 0.5×TBE) at 10 Watts at 4° C. RNA is visualized by staining with ethidium after electrophoresis.

C. Generation of dsRNA to Be Processed by Dicer:

1. To silence YFG the sequence or partial sequence must be known. A region can be selected that abides to the following rules.

a. Determining a Region to Target—

In one embodiment, a region about 100-150 nucleotides downstream of the ATG is selected, which prevents the d-siRNAs from having to compete with translation initiation proteins that bind mRNA. However, Green Fluorescent Protein (GFP) was silenced using the entire coding region as a target. Alternatively a region in the 3' UTR can be used and may have some advantages. In either case, usually a single gene is to be silenced so there is a worry about silencing several isoforms or silencing genes that are very similar. Therefore, the region should be lined up with isoforms and variants to make sure the silencing will be specific.

b. Determining the Size of the Target— r-Dicer will process 500 and 1000 bp dsRNAs into d-siRNAs. It is likely that Dicer will also process much larger dsRNAs, even a full-length cDNA. However, for silencing a single gene, a 500 bp dsRNA is sufficient.

2. To generate d-siRNAs, a large dsRNA corresponding to the target region is generated by in vitro transcription, thus a DNA template is made. This step can be done several ways, e.g., by making a PCR template with T7 promoters at both ends. Alternatively, the region of YFG can be subcloned into a transcription vector with in vitro promoters at both ends and digesting the plasmid after each promoter can generate template. The dsRNA can be made by annealing the single stranded (ssRNAs) or can be made by adding both enzymes to the in vitro reaction (e.g. add SP6 and T7 enzyme to single reaction). This method is more time consuming and possess no advantages unless YFG is already in a vector with promoters at each end and can easily be linearized to produce a template for the sense strand RNA (sRNA) and the antisense strand RNA (asRNA). dsRNA can be generated in a variety of other ways but the most efficient seems to be with PCR template with T7 promoter ends. Even if a full length cDNA of YFG is not available, the template can be generated from cDNA or a library.

a. Designing the Primers—

The primers used to produce a template contain a phage promoter sequence (T7, T3, or SP6) followed by gene specific sequence. T7 seems to produce the largest yield but the others also work.

SEQ ID NOs: 4 to 5

3. dsRNA is made with MegaScript (Ambion or equivalent from another company). The reaction is completed as recommended by manufacturer (include Dnase I treatment). For most of the dsRNAs tested, annealing occurs in the transcription reaction and can be monitored by electrophoresing the dsRNA in a 2% agarose gel. dsRNA will migrate like DNA, i.e., a 500 bp dsRNA will migrate at the same rate as a 500 bp band in a DNA ladder, whereas ssRNA will migrate much faster than a dsDNA of the equivalent size. It is possible that regions of some genes will not form dsRNAs during the transcription reaction. If this is the case RNA is then annealed directly after the transcription reaction by adding NaCl to 20 mM and Hepes to 10 mM, heating at 950 C for 1 min 30 sec, and then incubating at 37° C. for 1 hr. It is possible that strand scission may occur when heated in the presence of divalent ions such as $Mg^{2+}$. Therefore, EDTA would need to be added before heating. This is a problem because r-Dicer requires $Mg^{2+}$. Noticeable strand scission has not been detected and therefore, RNA is heated as described without adding EDTA. Alternatively RNA can be purified as described below prior to annealing, but annealing may not be as efficient (some regions may require divalent cations to anneal properly). Making RNA with Flourescein labeled-UTP, Dicing the dsRNA, and visualizing the cells after transfection can determine transfection efficiency.

```
                    5'-Primer and 3'-Primer
                                  +1
5' GCG TAATACGACTCACTATA          GG 18-21 gene specific nucleotides 3'
   Leader  T7 promoter sequence +1
5' GCG AATTAACCCTCACTAAA          GG 18-21 gene specific nucleotides 3'
   Leader  T3 promoter sequence +1
5' GCG ATTTAGGTGACACTATA          GA 18-21 gene specific nucleotides 3'
   Leader  SP6 promoter sequence
```

SEQ ID NOS: 1-3 b. Primer Example—

These are the primers were used to generate a template for cdc25c (accession number NM001790). cdc25c has two splice variants and variant 2 (accession number NM022809) is smaller because it lacks two regions. This template will determine if splice variants can be silenced even if only a portion of the d-siRNAs is targeting one variant.

D. Generation of d-siRNAs

1. Once dsRNA is made, in vitro dicing can be done. r-Dicer cleaves dsRNA slightly better if the dsRNA is purified. dsRNA can be purified by subsequent precipitations, first with LiCl and then with $NH_4OAC$ (as directed by Ambion). Alternatively if a large number of different d-siRNAs are desired, for example in a high-throughput screen, the purification step can be omitted because r-Dicer will cleave

```
                    5'-Primer and 3'-Primer
                                  +1
5' GCG TAATACGACTCACTATA          GG AGAGAGACACTTCCTTTACCG 3'
   Leader  T7 promoter sequence          99 bp from ATG +1
5' GCG TAATACGACTCACTATA          GG TATAGGCCACTTCTGCTCACC 3'
   Leader  T7 promoter sequence          634 bp from ATG
``` unpurified dsRNA, but cleavage is slightly less efficient as compared to purified dsRNA.

2. Reaction Conditions

| | |
|---|---|
| X µl | dsRNA (5 µg) |
| 9.0 µl | 10 mM ATP* |
| 4.5 µl | 50 mM MgCl$_2$ |
| 35.0 µl | Rxn Dil. Bfr.* |
| 10.0 µl | Enzyme |
| X µl | H$_2$O |
| 90.0 µl | |

*pH 8.0; Incubate @ 37° C. 18-22 hours
Note that the above volume can be scaled up as desired.

3. Several methods can be used to obtain pure d-siRNAs. r-Dicer, salts, buffer and leftover large dsRNA are removed.

a. "Cookbook" clean up. Using a series of spin columns large dsRNAs and r-Dicer are completely removed and most of the salts, NTPs and buffers are removed from the Dicer reaction. This produces d-siRNAs ready for transfection (in a minimal amount of salt, buffer, and NTP).

i. Desalt on G-25 spin column (Amersham, or equivalent from another company) after adding 10 µl of 100 mM EDTA to the 90 µl reaction. Manufacturers protocol followed (about 95% efficient).

ii. Extract protein using EZ-pure (Millipore). Manufacturers protocol followed-Spin 100 µl through, add 10 µl H$_2$O and spin again.

iii. Remove large dsRNAs with Microcon M-100 (Millipore) as directed by manufacturer. Note that the above protocol can be modified to replace steps (i) and (ii) with a precipitation step.

b. "Traditional" clean up. Using traditional methods recommended by Maniatis for nucleic acid purification and concentration r-Dicer, salts, NTPs and buffers can be almost completely removed. This produces a d-siRNAs ready for transfection.

i. Extract protein with phenol-chloroform-isoamyl alcohol (25:24:1) after addition of 10 µl of 100 mM EDTA to the 90 µl Dicer reaction. Proteinase K treatment is optional, but typically is unnecessary since only a small amount of protein is used in the reaction.

ii. Remove large dsRNAs with Microcon M-100 (Millipore) as directed by manufacturer.

iii. Precipitate by adding MgCl$_2$ to a final concentration of 10 mM, NH$_4$OAC to a final concentration of 0.75 M (Maniatis recommends 2-2.5 M, but this amount does not seem to be necessary), and 1 volume of Isopropanol (1 volume after the addition of salt). Vortex and spin a 14,000 RPM at 4° C. Chilling the solution does not seem to be necessary. Wash with 70% ethanol, dry and resuspend in nuclease free H$_2$O. It has not determined whether it is better to precipitate before or after the removal of large dsRNA.

c. Ambion spin columns-Using a series of spin columns d-siRNAs can be separated from r-Dicer, salts, buffer, and NTPs. This produces a d-siRNAs ready for transfection.

i. Add 10 µl of 100 mM EDTA to the 90 µl reaction and purify using the Ambion column as suggested by manufacturer. This step will remove r-Dicer, salts, buffer, and NTPs ii. Remove large dsRNAs with Microcon M-100 (Millipore) as directed by manufacturer.

iii. Note: it is possible that reversing the order of spin columns may result in a higher purity and yield of d-siRNAs, however this has not been tested.

d. After d-siRNAs are purified the concentration can be determined by measuring the absorbance at 260 nm. Typically 2.5 µg of d-siRNAs are obtained from 5 µg of dsRNA. The concentration of the d-siRNAs will depend on which method was used for purification. If the "cookbook" method is used, the concentration is usually 25 ng/µl. A higher concentration may be obtained by using a speed vac to decrease the volume or by using the "traditional" method and resuspending the d-siRNA in a small volume of H$_2$O. Note: when using the "cookbook" method there is residual ATP that absorbs at 260 nm, therefore an appropriate blank must be used. The blank is a reaction without RNA that has been purified using the "cookbook" method. In addition, a 15% native polyacrylamide gel (29:1, cast in 1× and electrophoresed in 0.5×TBE) should be ran as described above to ensure that the d-siRNAs are free of larger dsRNAs.

E. Transfect and assay for ablation of protein and appearance of a phenotype.

IV. CONCLUSION

The above demonstrates that recombinant Dicer can cleave large dsRNAs (.>500 base pairs) into a random pool of siRNAs (d-siRNAs) in vitro. The Dicer-generated d-siRNAs are capable of gene silencing in mammalian cell lines and are at least as effective as chemically synthesized siRNAs, and in some cases more effective. For commonly used mammalian cell lines, generating and using d-siRNAs is a more efficient and cost-effective method of gene silencing than the currently available techniques using single siRNAs (chemical synthesis, in vitro transcription, in vivo encoded hairpins) and introduces a new technology that will allow large-scale functional genomic screening. RNAi has become the method of choice for loss-of-function (lof) investigations in numerous systems including, *C. elegans, Drosophila*, fungi, plants, and even mammalian cell lines.

For loss-of-function investigations in mammalian cell lines, using d-siRNAs instead of single siRNAs has several advantages that are attributed to the fact that a pool of siRNAs is being used instead of a single siRNA. As previously mentioned using d-siRNAs, instead of single siRNAs, is cost-efficient and obviates the need to guess which 21-22 nucleotide sequence to target. In addition, single siRNAs would cause cleavage of the mRNA at a single site, possibly leaving the 3'-fragment to be translated as seen with antisense oligodoxynucleotides. These N-terminal truncated proteins may act as dominant negative or constitutively active truncation, potentially altering the true knock-out phenotype, whereas d-siRNAs will cause cleavage of the 500 nucleotide region targeted thereby decreasing the chances of translating a truncated fragment.

The method we describe here is simple and time-efficient such that within one week, a phenotype for "your favorite protein" may be determined. Recombinant Dicer may also allow pools or libraries of d-siRNAs to be generated and screened. This technology will allow large-scale functional genomic investigations in mammalian cell lines.

It is evident from the above results and discussion that the subject invention provides improved methods of producing siRNAs, as well as improved methods of using the produced siRNAs in various applications, including high throughput loss of function applications. As such, the subject invention makes the rapid determination of gene function possible. Accordingly, the present invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

contacting said dsRNA with a composition enriched for a Dicer protein having an activity that cleaves a dsRNA substrate into fragments having siRNA activity to produce said siRNA, wherein said Dicer protein includes dual RNase III motifs and said composition produces siRNAs from dsRNA and said composition converts at least 60% of said dsRNA to siRNA, and wherein said contacting occurs in the absence of ATP.

2. The method according to claim 1, wherein said method is in vitro.

3. The method according to claim 1, wherein said protein is a recombinantly produced protein.

4. The method according to claim 1, wherein said protein is full-length Dicer or an active fragment thereof.

What is claimed is:

1. A method for producing siRNA from an initial dsRNA, said method comprising:

5. The method according to claim 1, wherein siRNAs produced by said method range in length from about 20 to 23 residues.

6. The method according to claim 5, wherein siRNAs produced by said method are 20-21 residues in length.

7. The method according to claim 1, wherein said mammalian protein is human Dicer.

8. The method according to claim 1, wherein said DICER protein is present in an amount of at least about 40 ng/μl.

9. The method according to claim 1, wherein said DICER protein is present in an amount of at least about 160 ng/μl.

10. A method according to claim 1, wherein said Dicer protein is a recombinant Dicer protein.

11. A method according to claim 10, wherein said Dicer protein has an amino acid sequence at least 50% identical to the sequence of one of: human Dicer or drosophila Dicer.

12. A method according to claim 11, wherein said recombinant Dicer protein is human Dicer.

13. A method according to claim 12, wherein said human Dicer is human Dicer having accession number NM 030621.

14. A method according to claim 1, wherein said composition converts about 70% of said dsRNA to siRNA.

* * * * *